US00PP23450P2

(12) United States Plant Patent
Larsen

(10) Patent No.: US PP23,450 P2
(45) Date of Patent: Mar. 5, 2013

(54) ***OSTEOSPERMUM* PLANT NAMED 'SUNOST1103'**

(50) Latin Name: *Osteospermum ecklonis*
Varietal Denomination: Sunost1103

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 13/200,535

(22) Filed: Sep. 23, 2011

(51) Int. Cl.
*A01H 5/00* (2006.01)

(52) U.S. Cl. ..... Plt./360

(58) Field of Classification Search ..... Plt./360
See application file for complete search history.

*Primary Examiner* — Annette Para
(74) *Attorney, Agent, or Firm* — C. A. Whealy

(57) ABSTRACT

A new and distinct cultivar of *Osteospermum* plant named 'Sunost1103', characterized by its compact, outwardly spreading and mounding plant habit; freely branching growth habit; freely flowering habit; large daisy-type inflorescences with purple-colored ray florets; and good garden performance.

1 Drawing Sheet

Botanical designation: *Osteospermum ecklonis.*
Cultivar denomination: 'SUNOST1103'.

BACKGROUND OF THE INVENTION

The present invention relates to a new and distinct cultivar of *Osteospermum* plant, botanically known as *Osteospermum ecklonis*, and hereinafter referred to by the name 'Sunost1103'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive inflorescence coloration.

The new *Osteospermum* plant originated from a cross-pollination by the Inventor in May, 2008 of a proprietary selection of *Osteospermum ecklonis* identified as code number 05.50.018, not patented, as the female, or seed, parent with *Osteospermum ecklonis* 'Sunpix0804', not patented, as the male, or pollen, parent. The new *Osteospermum* plant was discovered and selected by the Inventor as a single flowering plant within the progeny of the stated cross-pollination in a controlled greenhouse environment in Odense, Denmark in June, 2009.

Asexual reproduction of the new *Osteospermum* plant by terminal cuttings in a controlled greenhouse environment in Odense, Denmark since November, 2009, has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunost1103'.

These characteristics in combination distinguish 'Sunost1103' as a new and distinct *Osteospermum* plant:

1. Compact, outwardly spreading and mounding plant habit.
2. Freely branching growth habit.
3. Freely flowering habit.
4. Large daisy-type inflorescences with purple-colored ray florets.
5. Good garden performance.

Plants of the new *Osteospermum* differ from plants of the female parent selection in the following characteristics:

1. Plants of the new *Osteospermum* are more compact than plants of the female parent selection.
2. Plants of the new *Osteospermum* are more freely branching than plants of the female parent selection.
3. Plants of the new *Osteospermum* have smaller leaves than plants of the female parent selection.
4. Plants of the new *Osteospermum* have lighter-colored ray florets than plants of 'Sheila'.

Plants of the new *Osteospermum* differ from plants of the male parent, 'Sunpix0804', primarily in ray floret color as plants of 'Sunpix0804' have darker-colored ray florets. In addition, plants of the new *Osteospermum* are not as compact as plants of 'Sunpix0804'.

Plants of the new *Osteospermum* can be compared to plants of the *Osteospermum* 'Sunny Mary', disclosed in U.S. Plant Pat. No. 16,389. In side-by-side comparisons conducted in Odense, Denmark, plants of the new *Osteospermum* differed from plants of 'Sunny Mary' in the following characteristics:

1. Plants of the new *Osteospermum* were more freely branching than plants of 'Sunny Mary'.
2. Plants of the new *Osteospermum* had smaller leaves than plants of 'Sunny Mary'.
3. Plants of the new *Osteospermum* and 'Sunny Mary' differed in ray floret color as plants of 'Sunny Mary' have darker-colored ray florets.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph at the bottom of the sheet comprises a side perspective view of three typical flowering plants of 'Sunost1103' grown in a 21.5-cm container.

The photograph at the top of the sheet is a close-up view of a typical flowering plant of 'Sunost1103'.

DETAILED BOTANICAL DESCRIPTION

The aforementioned photographs, following observations and measurements describe plants grown in Bonsall, Calif. during the summer in a polyethylene-covered greenhouse and under environmental conditions and cultural practices which approximate those generally used in commercial *Osteospermum* production. During the production of the plants, day temperatures ranged from 18° C. to 32° C., night temperatures ranged from 7° C. to 18° C. and light levels ranged from 7,000 to 8,000 foot candles. Plants were pinched twice and were six weeks old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'Sunost1103'.

Parentage:

*Female, or seed, parent*.—Proprietary selection of *Osteospermum ecklonis* identified as code number 05.50.018, not patented.

*Male, or pollen, parent*.—*Osteospermum ecklonis* 'Sunpix0804', not patented.

Propagation:

*Type*.—Terminal vegetative cuttings.

*Time to initiate roots, summer*.—About twelve days at 18° C.

*Time to initiate roots, winter*.—About two weeks at 18° C. to 20° C.

*Time to produce a rooted cutting, summer*.—About 20 days at 18° C. to 20° C.

*Time to produce a rooted cutting, winter*.—About four weeks at 18° C.

*Root description*.—Medium in thickness, fibrous; white in color.

*Rooting habit*.—Freely branching; medium density.

Plant description:

*Plant form/growth habit*.—Compact, outwardly spreading and mounding plant habit; inflorescences positioned above and beyond the foliar plane; moderately vigorous growth habit.

*Plant height*.—About 21.5 cm.

*Plant diameter*.—About 35 cm.

*Lateral branches*.—Quantity per plant: Freely branching habit with about ten primary lateral branches per plant; pinching enhances branching. Length: About 21 cm. Diameter: About 4 mm. Internode length: About 2.8 cm. Strength: Strong. Texture: Mostly smooth and glabrous with a few scattered hairs. Color: Close to 138B.

*Foliage description*.—Arrangement: Alternate, simple. Length: About 4.3 cm. Width: About 2.1 cm. Shape: Oblanceolate. Apex: Acute. Base: Attenuate. Margin: Broadly dentate to entire. Texture, upper surface: Smooth, glabrous; scaberulose; slightly pubescent along leaf margins. Texture, lower surface: Slightly pubescent; scaberulose. Venation pattern: Pinnate. Color: Developing leaves, upper surface: Close to N137B. Developing leaves, lower surface: Close to N137C. Fully expanded leaves, upper surface: Close to N137D; venation, close to 146B. Fully expanded leaves, lower surface: Close to 146A; venation, close to 146C. Petiole: Length: About 1.3 cm. Diameter: About 5 mm. Texture, upper and lower surfaces: Smooth, glabrous. Color, upper surface: Close to 146D. Color, lower surface: Close to 136D.

Inflorescence description:

*Appearance*.—Daisy-type inflorescence form with oblanceolate-shaped ray florets; inflorescences terminal and axillary and positioned above and beyond the foliar plane; disc and ray florets developing acropetally on a capitulum; inflorescences face mostly upright.

*Flowering habit*.—Freely flowering habit with about 45 inflorescences developing per plant.

*Fragrance*.—None detected.

*Flowering response*.—In southern California, plants of the new *Osteospermum* flower continuously from early spring to mid-summer; early flowering habit, plants begin flowering about six weeks after planting.

*Longevity*.—Inflorescences of the new *Osteospermum* last about three days on the plant; inflorescences persistent.

*Inflorescence bud*.—Height: About 2 cm. Diameter: About 1.1 cm. Shape: Ovate to oblong. Color: Close to 150C to 150D.

*Inflorescence size*.—Diameter: About 4.6 cm. Depth (height): About 1.8 cm. Disc diameter: About 1 cm. Receptacle diameter: About 1.2 cm. Receptacle height: About 1.1 cm.

*Ray florets*.—Length: About 2.6 cm. Width: About 6 mm. Shape: Oblanceolate. Apex: Broadly acute. Base: Attenuate. Margin: Entire. Aspect: About 45° from vertical. Texture, upper and lower surfaces: Smooth, glabrous; velvety. Number of ray florets per inflorescence: About 17 to 18 in a single whorl. Color: When opening, upper surface: Close to 84B. When opening, lower surface: Longitudinal stripes, close to 94C and 157D. Fully opened, upper surface: Midsection and towards the apex, longitudinal stripes, close to N78A and N78B; towards the base, close to 72A; color becoming closer to N79C with development. Fully opened, lower surface: Longitudinal stripes, close to N77B and 186C.

*Disc florets*.—Shape: Tubular; apex dentate, five-pointed. Length: About 8 mm. Diameter, apex: About 3 mm. Diameter, base: About 1.5 mm. Number of disc florets per inflorescence: About 80. Color: Immature: Close to 145A. Mature: Apex: Close to N79C. Midsection: Close to 145C. Base: Close to 145D.

*Phyllaries*.—Quantity per inflorescence: About 18 in a single whorl. Length: About 7 mm. Width: About 2 mm. Shape: Lanceolate. Apex: Acuminate. Base: Truncate. Margin: Entire. Texture, upper surface: Smooth, glabrous. Texture, lower surface: Pubescent. Color, upper surface: Close to 146C. Color, lower surface: Close to 146A.

*Peduncles*.—Length, terminal peduncle: About 8.8 cm. Diameter: About 1.5 mm. Strength: Strong. Aspect, terminal peduncles: Mostly upright. Aspect, axillary peduncles: About 30° to 35° from vertical. Texture: Sparsely pubescent. Color: Close to 144A.

*Reproductive organs*.—Androecium: Present on disc florets only. Filament length: About 1.5 mm. Filament color: Close to 157A. Anther shape: Oblong. Anther length: About 2 mm. Anther color: Close to 79A. Pollen amount: Scarce. Pollen color: Close to 164B. Gynoecium: Present on both ray and disc florets. Pistil length: About 6 mm. Stigma shape: Bi-parted. Stigma color: Close to N79A. Style length: About 2.5 mm. Style color: Close to N79B. Ovary color: Close to 145B.

*Seeds and fruits*.—Seed and fruit development has not been observed on plants of the new *Osteospermum*.

Disease and pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind, high temperatures of about 40° C. and to be hardy to USDA Hardiness Zone 9.

It is claimed:

1. A new and distinct *Osteospermum* plant named 'Sunost1103' as illustrated and described.

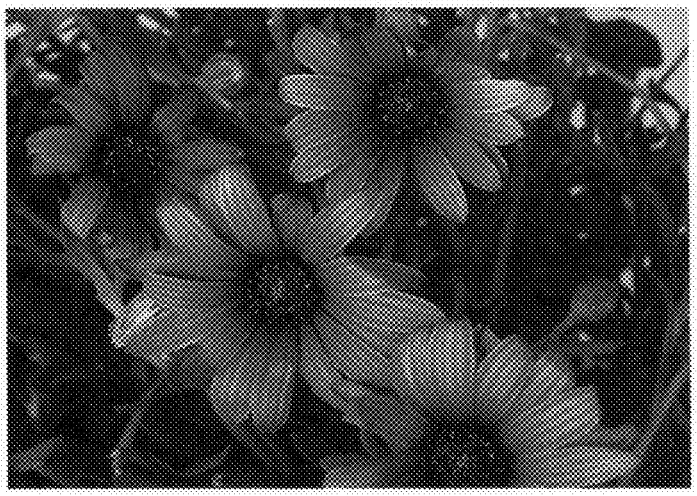
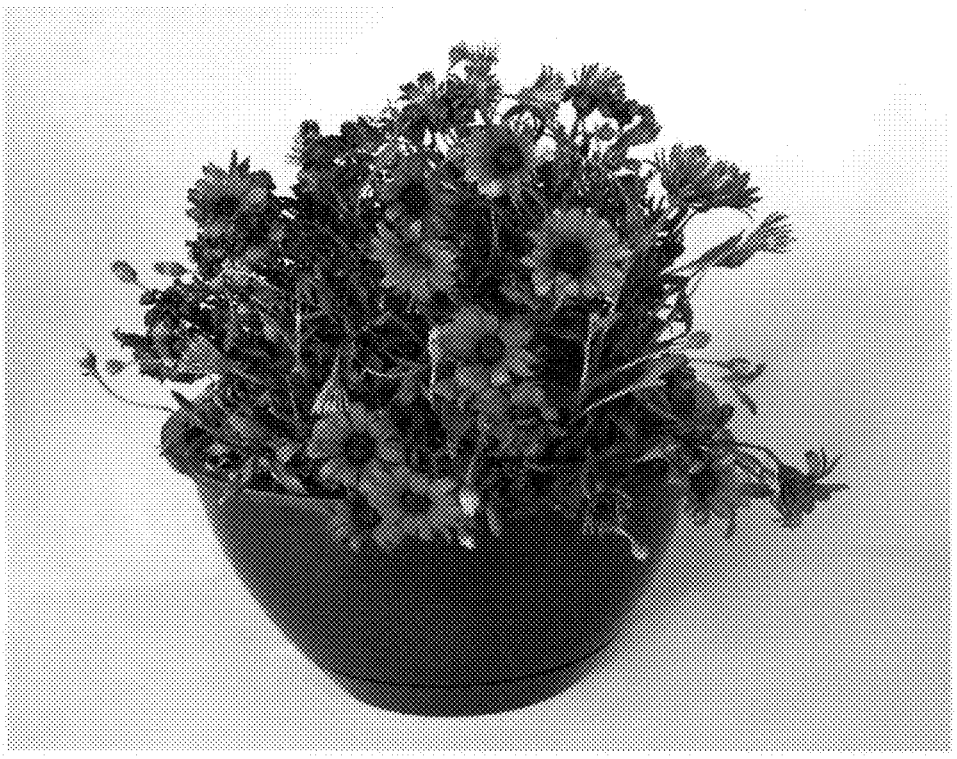

* * * * *